United States Patent
Guamis Lopez et al.

(10) Patent No.: US 9,192,190 B2
(45) Date of Patent: Nov. 24, 2015

(54) CONTINUOUS SYSTEM AND PROCEDURE OF STERILIZATION AND PHYSICAL STABILIZATION OF PUMPABLE FLUIDS BY MEANS OF AN ULTRA-HIGH PRESSURE HOMOGENIZATION

(75) Inventors: Buenaventura Guamis Lopez, Sant Cugat del Valles (ES); Antonio Jose Trujillo Mesa, Sant Feliu de Llobregat (ES); Victoria Ferragut Perez, Cerdanyola del Valles (ES); Joan Miquel Quevedo Terre, Barcelona (ES); Tomas Julio Lopez Pedemonte, Montevideo (UY); Martin Nicolas Buffa Dunat, Ripollet (ES)

(73) Assignee: UNIVERSITAT AUTONOMA DE BARCELONA, Bellaterra, Barcelona (ES)

( * ) Notice: Subject to any disclaimer, the term of this patent is extended or adjusted under 35 U.S.C. 154(b) by 80 days.

(21) Appl. No.: 13/811,199
(22) PCT Filed: Jul. 18, 2011
(86) PCT No.: PCT/EP2011/003572
§ 371 (c)(1),
(2), (4) Date: May 29, 2013
(87) PCT Pub. No.: WO2012/010284
PCT Pub. Date: Jan. 26, 2012

(65) Prior Publication Data
US 2013/0243644 A1 Sep. 19, 2013

(30) Foreign Application Priority Data
Jul. 21, 2010 (EP) .................................... 10380094

(51) Int. Cl.
*A61L 2/00* (2006.01)
*B01J 19/00* (2006.01)
(Continued)

(52) U.S. Cl.
CPC .............. *A23L 3/0155* (2013.01); *A23C 3/033* (2013.01); *A23L 3/18* (2013.01); *A61L 2/07* (2013.01)

(58) Field of Classification Search
CPC ........ A21D 6/003; C12H 1/00; B67C 7/0073; A23L 3/00; A23C 3/00
USPC ............ 422/1, 38, 41, 307; 99/451, 453, 470; 210/175; 134/22.12, 22.15
See application file for complete search history.

(56) References Cited

U.S. PATENT DOCUMENTS 6,136,362 A * 10/2000 Ashton .......................... 426/521
6,207,215 B1 3/2001 Wilson et al.
6,673,311 B1 * 1/2004 Sotoyama et al. ................. 422/1

FOREIGN PATENT DOCUMENTS

| EP | 1 027 835 | 8/2000 |
| JP | 59-210862 | 11/1984 |
| WO | WO 2006/110051 | 10/2006 |

OTHER PUBLICATIONS

Axelrod et al. "Lipoxygenase from Soybeans." *Methods in Enzymology*. 1981. 71:441-451.

(Continued)

*Primary Examiner* — Monzer R Chorbaji
(74) *Attorney, Agent, or Firm* — Merchant & Gould P.C.

(57) ABSTRACT

Continuous system and procedure of sterilization and physical stabilization of pumpable fluids, food, or other type of fluids, through ultra-high pressure homogenization (UHPH) includes a first heat exchanger 1 which preheats the fluid at temperature $T_p$ between 40 and 90° C.; an ultra-homogenizer 3 through which fluid at temperature $T_p$ is introduced at a pressure $P_u$ between 200 and 600 MPa increasing its temperature up to a final value $T_u$. A second heat exchanger 4 has its cooling temperature adjusted at value $T_e$. An aseptic tank 5 receives the cooled down fluid at value $T_e$, from which it is pumped by sterile air pressure into an aseptic packaging machine, for the packaging of the final product.

7 Claims, 1 Drawing Sheet

(51) Int. Cl.
A23C 3/07 (2006.01)
A23C 3/02 (2006.01)
A23L 3/015 (2006.01)
A23C 3/033 (2006.01)
A23L 3/18 (2006.01)
A61L 2/07 (2006.01)

(56) References Cited

OTHER PUBLICATIONS

Donsì et al., "High-Pressure Homogenisation for Food Sanitisation", *Proceedings of the 13th World Congress of Food Science and Technology 'Food is Life'*, Nantes, Sep. 17-21, 2006, pp. 1811-1822.

Donsì et al., "High-Pressure Homogenization for Food Sanitization", *Global Issues in Food Science and Technology*, Ed. Barbosa-Cánovas, G. et al. Academic Press. Burlington, MA, USA, Chapter 19, 2009, pp. 309-335.

Ferragut et al., "Physical characteristics during storage of soy yogurt made from ultra-high pressure homogenized soymilk", *Journal of Food Engineering*, vol. 92, 2009, pp. 63-69.

Gould, "New Methods of Food Preservation", Blackie: London, 1998, pp. 151-156.

Grácia-Juliá et al., "Effect of dynamic high pressure on whey protein aggregation: A comparison with the effect of continuous short-time thermal treatments", *Food Hydrocolloids*, vol. 22, 2008, pp. 1014-1032.

Guerrero-Beltran et al. "Pressure and temperature combination for inactivation of soymilk trypsin inhibitors." *Food Chem.* 2009 116:676-679.

Hamerstrand et al. "Tyrpsin Inhibitors in Soy Products: Modification of the Standard Analytical Procedure." *Cereal Chem.* 1981. 58(1):42-45.

International Search Report from International Application No. PCT/EP2011/003572 mailed Jan. 16, 2012, 3 pages.

Ostal et al. "Antioxidative Activity of Urate in Bovine Milk." *J. Agri Food Chem.* 2000. 48:5588-5592.

Pathanibul et al. "Inactivation of Escherichia coli and Listeria innocua in apple and carrot juices using high pressure homogenization and nisin." *Int J of Food Microbiology.* 2009. 129:316-320.

Vachon et al., "Inactivation of Foodborne Pathogens in Milk Using Dynamic High Pressure", *Journal of Food Protection*, vol. 65, No. 2, 2002, pp. 345-352.

Van der Ven et al. "Inactivation of Soybean Tyrpsin Inhibitors and Lipoxygenase by High-Pressure Processing." *J. of Agricultrual and Food Chem.* 2005. 53:1087-1092.

International Search Report for International Application No. PCT/EP2011/003572 mailed Jan. 16, 2012 (3 pages).

* cited by examiner

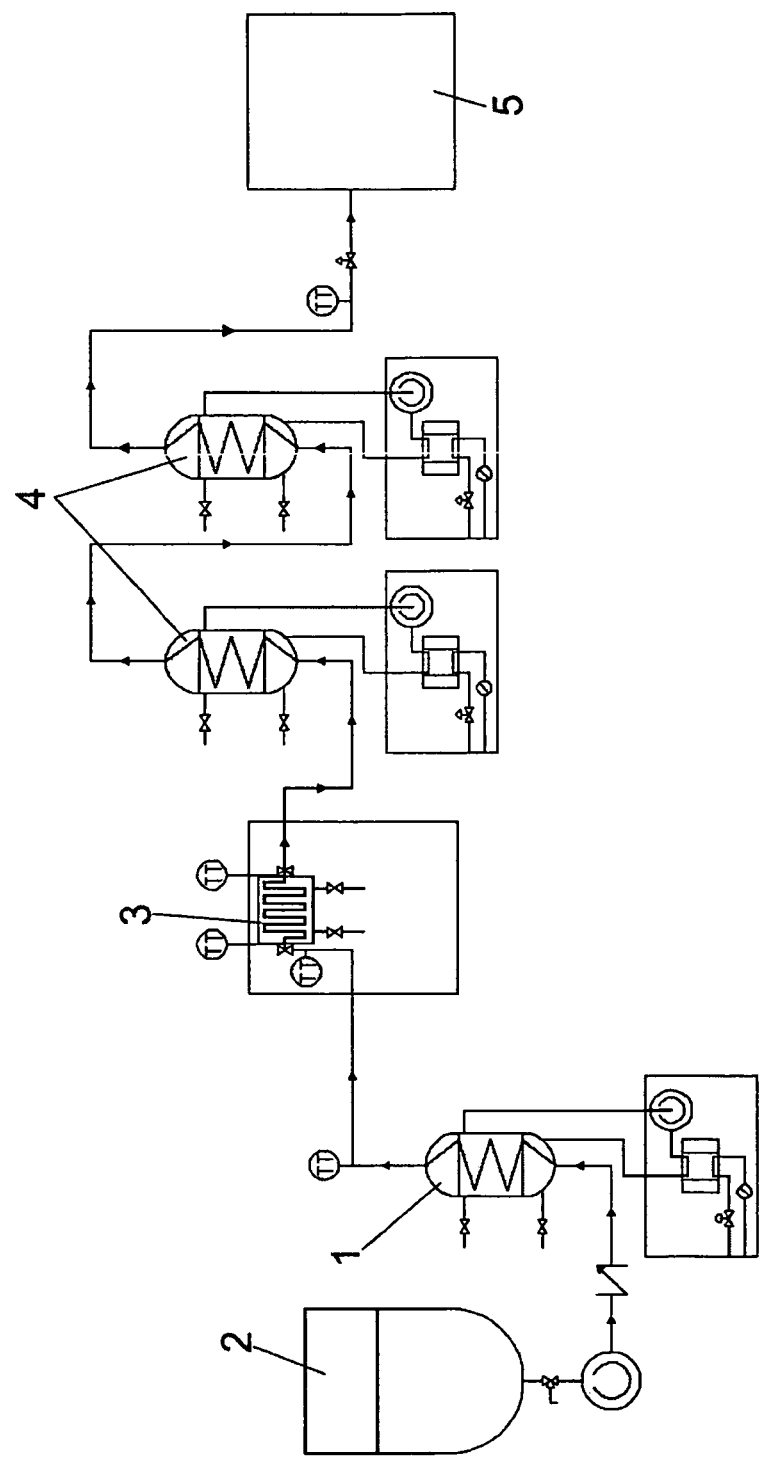

CONTINUOUS SYSTEM AND PROCEDURE OF STERILIZATION AND PHYSICAL STABILIZATION OF PUMPABLE FLUIDS BY MEANS OF AN ULTRA-HIGH PRESSURE HOMOGENIZATION

This application is a National Stage Application of PCT/EP2011/003572, filed 18 Jul. 2011, which claims benefit of Serial No. 10380094.2, filed 21 Jul. 2010 in Europe and which applications are incorporated herein by reference. To the extent appropriate, a claim of priority is made to each of the above disclosed applications.

FIELD OF THE INVENTION

The present invention refers to a continuous system and procedure of sterilization and physical stabilization of pumpable fluids by means of ultra-high pressure homogenization, which applies to the food, pharmaceutical, chemical and cosmetics sectors, and in general, to any pumpable product, chemically compatible with the system, obtaining a product susceptible to be aseptically packaged.

BACKGROUND OF THE INVENTION

Sterilization is a treatment that allows the destruction of vegetative forms and microbial spores and the prolonged conservation of a product stored at room temperature. Usually, heat treatments at higher temperatures than 100° C. are used. It is obvious that after a treatment with such conditions effects over the organoleptic properties can be seen, and in the case of food there can be important loses of nutritive value. On the other hand, many products cannot support these conditions and they physically destabilize. Food and other products sterilized by this system have a shelf life longer than six months (depending on its composition) if kept at room temperature. Sterilization process can be applied before or after packaging, requiring for each case different technologies as we will see later. Sterilization goes always along with food stabilization. In the case of solids, it is necessary to apply additives that protect colour and texture and strengthen flavour. In the case of liquid foods of colloidal nature, in order to avoid phase separation, mechanical treatments are employed such as the conventional homogenization and stabilizers are added (emulsifiers, feed thickeners, protectors for salt precipitation, etc.) depending on the food complexity.

In the case of sterilization of packed products, the heat treatment applies to the whole group of package and its content (food), and depending on the production requirements, a load system or a continuous one can be used.

When the food to be sterilized is a liquid the viscosity of which allows for it to be pumped, it is possible to use a sterilization system preceding packaging, associated to a subsequent aseptic packaging. In this case, the product circulates in a closed circuit in which there is a successive procedure of preheating, sterilization, cooling and aseptic packaging. Generally, sterilization is performed at high temperature: 135-150° C., which allows a very short time for processing: 4-15 sec. This treatment is usually known as Ultra High Temperature (UHT). UHT processes were implemented at industrial level on the 60's for liquid milk treatment, thus, obtaining products with characteristics more similar to the pasteurized milk than the ones obtained with conventional sterilizers that were used to sterilize bottled milk. From the 60's to the present day, others UHT processes have also been developed for other dairy products (concentrated milk, fresh cream, shakes, fermented products, ice creams, desserts . . . ) and for soups, sauces and purées, etc.

Compared with the sterilization of packed products, UHT process saves time, power, space and manpower. Nowadays, in the market there exist two UHT treatments: direct systems where the product is heated by direct contact with the heating medium (water steam), and indirect systems where heat is transmitted through a separation surface, in a heat exchanger.

In these sterilization processes and depending on the type of food, mainly on those that have an emulsion of the type oil in water (for example, milk, dipping sauces, shakes with dairy base or ice cream mix) it is necessary to introduce a homogenization process before or after the heat treatment. Homogenizers action reduces droplets size in the dispersed phase in order to stabilize the product in case there is a creaming phenomenon during its storage. Pressure homogenizers are built with a high pressure pump that works at 10-70 Mpa having a homogenization valve at the discharge side. When pumping liquid from the space between the valve and its support, the high pressure generated moves the liquid at high speed. At the valve end, the liquid movement speed drops abruptly and the extreme turbulence generated produces an intense shear rate. Other forces intervening in the process of reducing particle size are the collapsing of air bubbles (cavitation) and the impact forces created at the valves during the liquid trajectory. In some food, milk for example, there is sometimes an abnormal distribution of particles which produces additives. A second valve, similar to the first one and installed at the liquid trajectory, breaks these additives once more.

Heat treatment has, on the one side, beneficial effects over the food such as the microbial inactivation, however, in a parallel way; it generates undesired chemical and physicochemical changes, which can affect nutritional, organoleptic and/or technological properties depending on the applied treatment.

Flavour (aroma+flavour+consistency) is a very important parameter to consider as a quality aspect for the consumer of one of the most widely consumed sterilized food, such as milk, even more if it is consumed as a drink. Heat treatment has an important effect over milk flavour which can affect it in a higher or lower scale depending on the applied treatment intensity. An UHT sterilized milk (135-150° C., 2-20 s) is identified by a cooked aroma, mainly caused by the presence of $H_2S$ released after protein denaturalization, along with "caramel" aroma and another typical one associated to ketones formation. During a sterilization treatment in conventional bottle (105-120° C., 10-40 min) there is a strong cooked, ketone and caramel aroma, the later one caused by the formation of certain products from the Maillard reaction and caramelization products, which can even disguise cooked aroma. Other physical and biochemical phenomena these heat treatments can cause are product instability during its storage at room temperature due to protein precipitation, phases separation, creaming (separation of fat even though the product was previously homogenized), which makes it necessary for us to use certain additives such as emulsifiers, stabilizers or pH regulators in order to minimize or soften these effects derived from heat treatment. In less complex food, such as juices, there is a drastic loss of their vitamin content (vitamin C and other hydrosoluble vitamins), great alterations in their original flavour and aromas (volatile components loss), as well as changes in their colour.

Ultra High Pressure Homogenization (UHPH) Technology is based under the same principles as conventional homogenization with this one big difference that it can reach pressures higher than 200 Mpa, thanks to the valve design and the use of new materials. UHPH treatment can be associated to emerging physical techniques since its action results from combined forces of shear, turbulence, cavitation and impact caused by the application of dynamic high pressures. Nevertheless, this technology must not be mistaken with another technology that uses high pressures as well such as High Hydrostatic Pressure treatment (HHP). This technology, like UHPH, was developed as an alternative to the conventional heat treatments in the destruction of pathogenic and altering microorganisms, but the systems or work equipment as well as the mechanism of microbial inactivation which acts in this technology are totally different compared with UHPH as we will describe below. HHP equipment works with loads (discontinuous process) of product previously packed in flexible materials and closed guarantying their watertightness; this equipment is basically formed by a cylinder containing a pressure transmitting static fluid which is normally water (that is why it is called hydrostatic), a pressure generating system (low pressure pump and pressure intensifier). In this technology, packed food is introduced in the pressure cylinder filled with the pressure transmitting liquid (usually water) until selected pressure conditions are met, 400-1000 Mpa; (in industrial equipment of food applications up to 600 Mpa), and it is kept during the desired time. During this time, pressure is isostatically transmitted, which implies that the product is treated by homogenization, regardless its shape or size, and at the same time it prevents its deformation during the treatment. Then, after depressurising the cylinder, it is opened in order to extract the product from the machine.

As regards microbial inactivation mechanisms, HHP technology can inactivate microorganisms inducing changes in their morphology, biochemical reactions, genetic mechanisms or in their cell membrane. Normally, spores resist these treatments unless treatments combined with high temperatures are applied.

UHPH equipment developed so far are capable of processing fluids or pumpable food systems up to pressures of 400 MPa working in continuous processes. Up to now, different high pressure homogenization equipment has been employed in the chemical and pharmaceutical industries, specially food and biotechnology in order to emulsify, diffuse, mix and process their products.

In ultra-homogenizers, the homogenization valve is made with materials (such as ceramics) which are able to withstand pressures of up to 400 MPa (and its evolution to reach even higher pressures is probable) and temperatures over 100° C. Furthermore, the geometry of the valves is different from the classic APV-Gaulin valve found in conventional homogenizers.

This technology produces the disruption of dispersion particles including microorganisms. Particles can have a varied nature and are common in colloidal food such as milk, vegetables shakes, cloudy juices, etc. Among possible physical processes implied in microbial breakdown (main mechanism of microbial inactivation) during UHPH we can find: sudden pressure drop, impact forces, cut and torsion, turbulence and cavitation. The temperature increase of the product after passing through the valve contributes to microbial inactivation (including spores), since it is an additive effect to the physical forces developed at the homogenizer valve.

Even though we can consider UHPH technology as an alternative to the heat treatments, during UHPH process there is a marked increase of the product temperature due to: (1) the pressure increase occurring inside the intensifier and in the pipes located before the valve which generate a compression of the fluid and (2) the forces to which the fluid is subjected when passing through the high pressure valve and the conversion of kinetic energy into heat energy.

The pressure increase preceding the homogenization stage and the friction caused by the fluid high speed elevate product temperature approximately 2-2.5° C. every 10 MPa (a temperature increase of 20° C. to 50° C. in a homogenization cycle of 150 MPa). However, this heat effect, which applies in ultra-short periods (<0.5 s) can optionally be cancelled or minimized to the maximum by introducing a cooling equipment which, after the product pressure drop, controls temperature in a quick and efficient way. Likewise, that temperature increase caused by the homogenization cycle could be favoured and maximized if we expose the product to 40-90° C. temperatures, getting even sterilization temperatures (up to 150° C.), in flash way, after the first homogenization stage.

As regards the UHPH technology application in food fluids, it has been suggested that this treatment can cause pasteurization of several products such as milk, vegetable shakes, eggs, juices, etc. (Donsi, F., Ferrari, G., & Maresca, P. 2009. *High-Pressure Homogenization for Food Sanitization*. Chapter 19, pages 309-335. 2 In: Global Issues in Food Science and Technology. Ed. Barbosa-Cánovas, G. et al. Academic Press. Burlington, Mass., USA.). However, employed equipment and processes have shown to be insufficient to reach the sterilisation of studied products. For instance, Puig et al. (2008) studied the effect of UHPH treatment (200 MPa, inlet temperature 6-8° C.) over the microbiological and physicochemical characteristics of grape must, obtaining a residual microbiota in the product but with excellent sensory characteristics. Donsi et al (*High-Pressure Homogenisation for Food Sanitisation*. Proceedings of the 13th World Congress of Food Science and Technology 'Food is Life', Nantes, 17-21 Sep. 2006, 1851-1862, doi:10.1051/IUFoST:20060497) studied the effect of different UHPH cycles at 250 MPa in orange, apple and pineapple juices, evaluating microbial inactivation and quality loss of such treated products. UHPH was an effective treatment for obtaining pasteurized fruit juice, thus extending their shelf life and keeping their sensory characteristics for 28 days, refrigerating the product at 4° C.

Other researchers have suggested the addition of antimicrobial components to improve microbial inactivation produced by a UHPH treatment. In that way, Pathanibul et al. (2009. *Inactivation of Escherichia coli and Listeria innocua in apple and carrot juices using high pressure homogenization and nisin*. International Journal of Food Microbiology 129, 316-320.) studied the addition of nisin (0-10 Ul/ml) in apple and carrot juice inoculate with *Escherichia coli* or *Listeria innocua* (~7 log ufc/ml) and treated by UHPH (0-350 MPa), they observed important microbial reductions (~5 log ufc/ml) but their complete elimination was not reached.

The problem of ultra-homogenizers is that they do not guarantee by themselves the sterilization and subsequent packaging of food in aseptic conditions. That is to say, it is necessary to combine a series of equipment in a "System" which allows the sterilization (including the destruction of resistance spores), the stabilization without additives or with a higher control of their concentration and the packaging in aseptic conditions.

DESCRIPTION OF THE INVENTION

The system and procedure described herein allow (1) treatment and conservation of food and products of different nature which are pumpable (even heat sensitive ones) reaching at the end of the treatment the product commercial sterility, (2) product stabilization without using additives (or by reducing their concentration to the minimum), (3) avoidance of precipitation, minimizing, for instance denaturalization and protein addition, (4) avoidance of phase separation due to its intensive homogenizer effect and (5) maintenance of the original color, flavor and aromas of the treated food due to a minimum heat effect, which along with the homogenizer effect produces the product sterilization, safeguarding product organoleptic and nutritional characteristics and solving current problems of conventional sterilization and UHT. The heat effect produced on the food fluid when it passes through the ultra-homogenizer is reduced to the minimum by introducing cooling equipment, which, after the pressure drop, adjusts its temperature in a quick and efficient way.

The term "commercial sterility" is used in this context to refer to a food product in which conditions achieved during the treatment application produce food free of viable microbial forms with a significant effect on public health, and free of microbial forms without a significant effect on public health which may be able to reproduce themselves in food under normal storage and distribution conditions. On the other hand, it is understood that the food preparation and conditioning is done under sanitary conditions and these ordinary foods will not contain an excessive number of microorganisms. An important aspect of commercial sterility is that there can be living microorganisms in low quantities in the final packaged and sterilized product, but when the product is stored during reasonably long periods, microorganisms will not grow and food will remain safe and eatable.

According to a first aspect, there is provided a continuous system of sterilization and stabilization of pumpable, food, or other nature fluids, through ultra-high pressure homogenization (UHPH), being such fluids compatible with the materials that constitute the system (mainly, stainless steel).

Such system comprises the following treatment equipment: (1) a first heat exchanger which preheats the fluid, eatable or not, at temperature $T_p$ between 40 and 90° C., said fluid (between 0 and 39°) coming from a storage tank; (2) an ultra-homogenizer with a valve capable of working at high pressures through which, previously heated fluid at temperature $T_p$ is introduced at a pressure $P_u$ between 200 and 600 MPa, thus increasing fluid temperature up to a final value $T_u$, that is proportional to temperature $T_p$ and to pressure $P_u$ applied in such ultra-homogenizer; (3) at least one second heat exchanger in which the temperature of the fluid coming from the ultra-homogenizer is reduced to a desired cooling temperature value $T_e$, which will depend on the final product technology and (4) an aseptic tank that receives the cooled fluid to temperature value $T_e$, and from which the fluid is pumped into an (5) aseptic packaging machine.

After coming out from the ultra-homogenizer valve, final value of fluid temperature $T_u$ is kept during 0.1-1 s. Optionally, and if it is necessary, a fluid retention can be performed at final temperature $T_u$ during a period longer than 1 s.

At the second heat exchanger, the desired cooling temperature value $T_e$ of the fluid depends on its technology. That is to say, a cooling temperature value of 20-25° C. for non-gelatinized products and a value of 55° C. for products that gelatinize inside the package, such as, custards, puddings, etc.

According to a second aspect, there is also provided a procedure of sterilization and stabilization of pumpable fluids, food or other type of fluids, through ultra-high pressure homogenization, from a continuous system that comprises a first heat exchanger for pre heating, from which the preheated fluid is sent to an ultra-homogenizer that works at 200-600 MPa; a second heat exchanger for cooling the fluid after passing through the ultra-homogenizer; an aseptic tank which receives the cooled food and from which it is pumped to an aseptic packaging machine.

The procedure, innovatively, comprises the following stages based on said continuous system:

a pre sterilization of the sub system which comprises the ultra-homogenizer up to its connection with the aseptic tank, in which water is introduced in the system and pressure is raised up to 300-600 MPa, the ultra-homogenizer stops and the fluid inlet is closed, then water steam is added until it reaches a temperature of 140° C., keeping such temperature during 30-60 min; and pre sterilization of the aseptic tank by means of an steam injection process until it reaches a temperature of 140° C., keeping such temperature during 30-60 min, and double jacket cooling, keeping a positive pressure with sterilized air through filters (between 0.2 and 0.4µ) at a pressure of 0.4-6 bars.

once the system is "operating", that is to say, when the system is working with water in a continuous and stable manner at the selected temperature and pressure, the fluid pushes water and passes through the first preheating exchanger, it is introduced at a preheating temperature $T_p$ between 40 and 90° C. and at a pressure $P_u$ between 200 and 600 MPa, in the ultra-homogenizer valve, until achieving temperature $T_u$, which is kept after its coming out from the valve during 0.1-1 s.

after staying in the ultra-homogenizer, the fluid is cooled down through the refrigerating exchanger, where its cooling temperature is adjusted at a desired value $T_e$, that depends on the product technology. That is to say, a cooling temperature value $T_e$ of 20-25° C. for non-gelatinized products and a value of 55° C. for products that gelatinize inside the pack, such as, custards, puddings, and the like. Afterwards, the fluid is sent to the aseptic tank from which it is pumped and lately packaged in an aseptic packaging machine.

Besides being possible to sterilize the system with water steam due to its design, it can also be cleaned with conventional neutral detergents or with enzymatic detergents compatible with used materials.

The system simultaneously allows the sterilization of a liquid food, destroying microbial vegetative forms and spores, achieving physical stabilization (avoids precipitation and separation of components such as creaming), formation of nanocapsules by incorporating bioactive components, it also reduces protein allergenicity and all that while keeping the natural colour, its flavour (even improving it) and the nutritive value with a fresh product look.

The aforementioned also applies to cosmetics and medicine.

BRIEF DESCRIPTION OF THE DRAWINGS

In order to understand the invention better, the following is a brief description of a drawing specifically relating to an embodiment of the invention presented as a non-limitative example thereof.

FIG. 1 shows a diagram of the system described herein, which combines a series of equipment in a specific order with certain conditions to sterilize pumpable fluids.

EMBODIMENT

The following is an illustrative, non-limitative example of the invention. For all practical purposes, UHPH treatment of soymilk will be used as an example, since the elaboration procedure of the base product does not vary from the conventional one. However, the elaboration procedure of the soymilk (base product) from 100 Kg of soy beans is described:

Cleaning and hydration of soy bean (15 h room temperature),

Crushing (80-85° C. during 20 min.),

Passing through colloidal mill

Filtration and
Obtaining the raw sample of soymilk

Soymilk composition (average (% p/p)±standard deviation) obtained through the described procedure, using soy seed (*Glicine max*) from Majesta variety was: 5.78±0.47 of dry matter; 1.36±0.22 of total lipids and 3.10±0.15 of gross protein.

Raw sample is subjected to the system and procedure of the present invention, in the following optimal conditions:
  a) Pre-sterilization of system made up by heat exchangers (1 and 4), ultra homogenizer, aseptic tank and aseptic packaging machine,
  b) Preheating of soymilk coming from a storage tank (2) through a first heat exchanger (1) at a temperature Tp of 75° C., for its subsequent introduction in an ultra-homogenizer (3),
  c) The treatment of soymilk is performed at the ultra-homogenizer (3) at a pressure $P_u$ of 300 MPa. In these pressure conditions, soymilk gets to temperature $T_u$ of 130-137° C. during 0.5 s,
  d) Instant cooling through a heat exchanger (4) up to a temperature lower than 26° C. Two heat exchangers are employed in this example.
  e) Sending of the cooled fluid to an aseptic tank (5) for its subsequent packaging in an aseptic packaging machine.

In order to demonstrate that the system and stages obtain the optimal conditions of the ultra-high homogenization pressure treatment of soymilk, which suppose its commercial sterilization with excellent quality characteristics, we provide the details of a studied carried out. This supposes the comparative analysis of a total of three individual productions among different conditions of UHPH treatment and of conventional heat treatments such as, pasteurization and UHT sterilization starting from the same base product. The parameters analysed were the most outstanding ones in the product quality.

Treatment Conditions
Thermal Pasteurization:
  95° C./30 s, with 1 stage homogenization at 18 MPa.
UHT Treatment:
  142° C./6 s, with 2-stage homogenization (18 and 4 MPa).
UHPH:
  as shown in Table 1.

TABLE 1

UHPH tested conditions

| Treatments | Inlet T (° C.) | Valve T (° C.) | Outlet T (° C.) |
|---|---|---|---|
| 300 MPa | 55 | 127 | 26 |
| 200 MPa | 55 | 106 | 26 |
| 300 MPa | 65 | 130 | 25 |
| 200 MPa | 65 | 111 | 26 |
| 300 MPa | 75 | 137 | 25 |
| 200 MPa | 75 | 119 | 23 |

Microbiological Tests

Due to the characteristics of raw material (soy beans) derived from its origin and its subsequent manipulation, present pathogen microorganisms to be considered are those that ecologically have a high resistance to certain enterobacteriaceae among which certain ones must be considered as pathogen such as *Salmonella* spp, certain micrococcaceae such as, *Staphylococcus aureus*, yeasts and fungus, as well as sporulating microorganisms among which *Bacillus cereus* must be stressed due to its pathogen character, or due to its effect in the alteration of products into *B. subtilis* or *B. mesenteroides*.

Evaluation of Oxidation
Formation of Hydroperoxides

Hydroperoxides determination was performed in the fresh sample in a 24-hour period and after 15 days of storage at 4° C. The method used was the method described by Ostdal, et al. (2000). H., Andersen, H. J., & Nielsen, J. H. (2000). Antioxidative activity of urate in bovine milk. *Journal of Agriculture and Food Chemistry* 48, 5588-5592.

Lipoxigenase (LOX) Activity

To obtain the LOX extract we used the methodology described by: Axelrod, B., Cheesbrough, T. M., & Laasko, S. (1981). Lipoxygenase from soybean. Methods in enzimology. Ed. J. M. Lowenstein. Waltham, Mass. pp. 441-451. And LOX activity was determined through the use of the methodology described by Van der Ven, C., Matser, A. M., & Van den Berg, R. W. (2005). Inactivation of soybean trypsin inhibitors and lipoxygenase by high-pressure processing. *Journal of Agricultural and Food Chemistry* 53, 1087-1092.

Physical Stability

Physical stability was determined by two methods:

Centrifugation and determination of the percentage in weight of the sediment layer.

In bottles through the qualitative evaluation of the sediment layer at storage (2, 5 and 7 days).

Particle Size

It was determined by dispersion of laser light in a Beckman Coulter LS™ 13320 analyser, which allows the detection of particles or droplets of a diameter between 0.04 and 2000 μm.

Activity of Trypsin Inhibitor (TIA)

TIA extracts and the analytics were found and analysed through the methodologies described by: Guerrero-Beltrán, J. A., Estrada-Girón, Y., Swanson, B. & Barbasa-Cánovas, G. V. (2009). Pressure and temperature combination for inactivation of soymilk trypsin inhibitors. *Food Chemistry* 116, 676-679., and Hamerstrand, G. E., Black, L. T., & Glover, J. D. (1981). Trypsin-inhibitors in soy products—Modification of the standard analytical procedure. *Cereal Chemistry* 58, 42-45.

Results

TABLE 2

Microbiological recount (log UFC/ml) in soymilk (Average ± standard variation)

| Treatment | Mesophile recount | Spores | Enterobacteriaceae | Molds | Yeasts |
|---|---|---|---|---|---|
| Raw | 7.84 ± 0.11 | 4.94 ± 0.16 | 2.57 ± 0.02 | 1.60 ± 0.00 | 2.96 ± 0.07 |
| Pasteurized | 4.93 ± 0.07 | 3.67 ± 0.58 | ND | ND | ND |
| UHT | ND | ND | ND | ND | ND |
| 200 MP, 55° C. | 5.29 ± 0.25 | 1.61 ± 0.12 | ND | ND | ND |

TABLE 2-continued

Microbiological recount (log UFC/ml) in soymilk (Average ± standard variation)

| | | | | | |
|---|---|---|---|---|---|
| 200 MP, 65° C. | 4.51 ± 0.34 | 1.50 ± 0.21 | ND | ND | ND |
| 200 MP, 75° C. | ND | ND | ND | ND | ND |
| 300 MP, 55° C. | ND | ND | ND | ND | ND |
| 300 MP, 65° C. | ND | ND | ND | ND | ND |
| 300 MP, 75° C. | ND | ND | ND | ND | ND |

| Treatment | S. aureus | B. cereus | Salmonell | Incubation at 30° C. (1st week)[a] |
|---|---|---|---|---|
| Raw | ND | 6.35 ± 0.01 | ND | |
| Pasteurized | ND | 4.87 ± 0.17 | ND | |
| UHT | ND | ND | ND | − |
| 200 MP, 55° C. | ND | 4.08 ± 0.19 | ND | + |
| 200 MP, 65° C. | ND | 3.40 ± 0.12 | ND | + |
| 200 MP, 75° C. | ND | ND | ND | + |
| 300 MP, 55° C. | ND | ND | ND | + |
| 300 MP, 65° C. | ND | ND | ND | + |
| 300 MP, 75° C. | ND | ND | ND | − |

ND: not detected
[a](+) Bacterial growth and coagulation of the sample: (−) Without bacterial growth

TABLE 3

Average values (±d.e) of hydroperoxides (absorbance), lipoxigenated activity (LOX), percentage of the residual activity of trypsin inhibitors in relation to the raw sample and pH.

| Treatment | hydro-peroxides 0 day | (abs) 15 days | LOX | TIA(residual activity %) | pH |
|---|---|---|---|---|---|
| Raw | 0.917 ± 0.07 | 0.956 ± 0.04 | ND | 100.0 | 6.69 ± 0.01 |
| Pasteurized | 0.943 ± 0.04 | 1.257 ± 0.01 | ND | 91.4 | 6.73 ± 0.01 |
| UHT | 0.801 ± 0.03 | 0.681 ± 0.03 | ND | 69.9 | 6.79 ± 0.01 |
| 300 MP, 55° C. | 0.676 ± 0.09 | 0.996 ± 0.03 | ND | 65.0 | 6.69 ± 0.01 |
| 200 MP, 55° C. | 0.947 ± 0.03 | 1.028 ± 0.02 | ND | 61.2 | 6.70 ± 0.01 |
| 300 MP, 65° C. | 0.700 ± 0.01 | 0.655 ± 0.01 | ND | 66.0 | 6.71 ± 0.01 |
| 200 MP, 65° C. | 1.007 ± 0.01 | 1.024 ± 0.08 | ND | 54.9 | 6.69 ± 0.01 |
| 300 MP, 75° C. | 0.671 ± 0.07 | 0.588 ± 0.01 | ND | 64.1 | 6.72 ± 0.01 |
| 200 MP, 75° C. | 0.921 ± 0.01 | 0.963 ± 0.05 | ND | 63.0 | 6.69 ± 0.01 |

TABLE 4

Physical stability. Average percentage (±d.e) of sedimentation by centrifugation

| | Physical stability (%) | |
|---|---|---|
| Treatment | day 1 | day 15 |
| Raw | 12.07 ± 3.26 | 9.06 ± 0.27 |
| Pasteurized | 11.75 ± 1.06 | 4.58 ± 0.02 |
| UHT | 7.80 ± 1.09 | 4.28 ± 0.16 |
| 300 MP, 55° C. | 1.88 ± 0.27 | 1.71 ± 0.03 |
| 200 MP, 55° C. | 1.37 ± 0.09 | 1.57 ± 0.02 |
| 300 MP, 65° C. | 1.93 ± 0.09 | 1.63 ± 0.05 |
| 200 MP, 65° C. | 1.43 ± 0.06 | 1.73 ± 0.10 |
| 300 MP, 75° C. | 1.52 ± 0.17 | 1.48 ± 0.10 |
| 200 MP, 75° C. | 1.47 ± 0.08 | 1.63 ± 0.03 |

TABLE 5

Physical stability. Static sedimentation values.

| | Height of the formed layer (mm) | | |
|---|---|---|---|
| Treatment | day 2 | day 5 | day 7 |
| Raw | 7.0 | 9.0 | 9.0 |
| Pasteurized | 2.0 | 3.0 | 3.0 |
| UHT | 5.0 | 5.0 | 5.0 |
| 300 MP, 55° C. | ND | ND | ND |
| 200 MP, 55° C. | ND | ND | ND |
| 300 MP, 65° C. | ND | ND | ND |
| 200 MP, 65° C. | ND | ND | ND |
| 300 MP, 75° C. | ND | ND | ND |
| 200 MP, 75° C. | ND | ND | ND |

ND: Not Detected

TABLE 6

Average size of soymilk particles.

| Treatment | $D_{10}$ μm | $D_{50}$ μm | $D_{90}$ μm |
|---|---|---|---|
| Raw | 1.05 ± 0.02 | 10.44 ± 0.20 | 26.92 ± 1.69 |
| Pasteurized | 5.57 ± 2.07 | 45.12 ± 9.48 | 99.04 ± 18.0 |
| UHT | 0.23 ± 0.00 | 2.24 ± 0.07 | 37.87 ± 1.47 |
| 300 MP, 55° C. | 0.10 ± 0.00 | 15.23 ± 1.11 | 54.72 ± 6.34 |
| 200 MP, 55° C. | 0.08 ± 0.00 | 0.15 ± 0.01 | 32.04 ± 8.59 |
| 300 MP, 65° C. | 0.09 ± 0.00 | 6.87 ± 0.69 | 33.62 ± 2.44 |
| 200 MP, 65° C. | 0.12 ± 0.00 | 28.58 ± 0.63 | 66.49 ± 1.82 |
| 300 MP, 75° C. | 0.10 ± 0.00 | 8.88 ± 0.47 | 38.03 ± 1.85 |
| 200 MP, 75° C. | 0.11 ± 0.00 | 18.12 ± 0.67 | 45.58 ± 2.92 |

$D_{10}$ μm: is the diameter below which there is the 10% of particles volume fraction;
$D_{50}$ μm: is the diameter below which there is the 50% of particles volume fraction;
$D_{50}$ μm: is the diameter below which there is the 90% of particles volume fraction.

CONCLUSIONS

Soymilk treatment, through the system proposed in the patent application, with an inlet temperature to the ultra-homogenizer of 75° C. and a pressure of 300 MPa achieves:
  Product sterilization.
  Great physical stability during product precipitation and spontaneous skimming.
  Lower oxidation level (contained in hydroperoxides) than the product obtained with an UHT sterilization treatment.

Similar levels of trypsin inhibitors (digestibility) in relation to UHT.

More tasteful products than the UHT treated (details not shown), which means that "herb" and "bean" flavours are more reduced.

The invention claimed is:

1. Continuous system of sterilization and physical stabilization of pumpable fluids, food or other type, through ultra-high pressure homogenization (UHPH), comprising:
   a first heat exchanger which preheats fluid coming from a storage tank at temperature $T_p$ between 40 and 90° C.;
   an ultra-homogenizer including a high pressure valve through which pre heated fluid at temperature $T_p$ is introduced at a pressure $P_u$ between 200 and 600 MPa, thus increasing the fluid temperature up to a final value $T_u$, which is proportional to temperature $T_p$ when entering the high pressure valve and to applied pressure $P_u$;
   at least one second heat exchanger in which the temperature of the fluid coming from the ultra-homogenizer is adjusted up to a desired cooling temperature value $T_e$; and
   an aseptic tank that receives the cooled fluid at value $T_e$, and from which the fluid is pumped by sterile air pressure into an aseptic packaging machine, to pack a final product.

2. A continuous system of sterilization and physical stabilization according to claim 1, wherein the final value of temperature $T_u$ is kept during 0.1-1 s.

3. A continuous system of sterilization and physical stabilization according to claim 1, wherein the fluid cooling temperature, after passing through the second heat exchanger, is 20-25° C., for non-gelatinized products.

4. A continuous system of sterilization and physical stabilization according to claim 1, wherein the fluid cooling temperature, after passing through the second heat exchanger, is 55° C. for products that gelatinize inside the pack.

5. Procedure of sterilization and physical stabilization of pumpable fluids, food, or other type of fluids, through ultra-high pressure homogenization, from a continuous system that includes a first heat exchanger for pre heating, from which preheated fluid is sent to an ultra-homogenizer that has a high-pressure valve, where the fluid is introduced at pressures between 200 and 600 MPa; at least one second refrigerating exchanger to reduce fluid temperature after coming out from the ultra-homogenizer; an aseptic tank which receives the cooled food and from which the cooled food is pumped to an aseptic packaging machine, comprising:
   a stage of pre-sterilization of the system which comprises the ultra-homogenizer-up to connection with the aseptic tank, in which water is introduced in the system and pressure is raised up to 300-600 MPa, the ultra-homogenizer stops and a fluid inlet is closed, then water steam is added until the water stream reaches a temperature of 140° C., keeping the temperature during 30-60 min; and pre-sterilization of the aseptic tank by a steam injection process until the aseptic tank reaches a temperature of 140° C., keeping the temperature during 30-60 min, and double jacket cooling, keeping a positive pressure with sterilized air through filters at 0.4-6 bars of pressure,
   once the system is working with water in a continuous and stable manner at the selected temperature and pressure for the fluid treatment, and after passing through the first preheat exchanger 1, the fluid is introduced at a temperature $T_p$ between 40 and 90° C. and at a pressure $P_u$ between 200 and 600 MPa, in the ultra-homogenizer valve, so the fluid achieves a temperature $T_u$, which is kept after coming out from the valve during 0.1 to 1 s, and
   after staying in the ultra-homogenizer, the fluid is cooled down through the refrigerating exchanger, where cooling temperature is adjusted at value $T_e$, depending on the product, the fluid is then sent to the aseptic tank, from which the fluid is pumped and lately packaged in an aseptic packaging machine.

6. The procedure of sterilization and physical stabilization according to claim 5, wherein the fluid is cooled down to a temperature $T_e$ of 20-25° C. for non-gelatinized products.

7. The procedure of sterilization and physical stabilization according to claim 5, wherein the fluid is cooled down to a temperature $T_e$ of 55° C. for products that gelatinize inside the package.

* * * * *